United States Patent
Ito et al.

(10) Patent No.: US 10,336,882 B2
(45) Date of Patent: *Jul. 2, 2019

(54) METHOD OF RECOVERING LACTIDE

(71) Applicant: Toyo Seikan Co., Ltd., Tokyo (JP)

(72) Inventors: Takuro Ito, Tokyo (JP); Junko Tanabe, Yokohama (JP); Tomoaki Taguchi, Yokohama (JP)

(73) Assignee: TOYO SEIKAN CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/779,911

(22) PCT Filed: Dec. 7, 2016

(86) PCT No.: PCT/JP2016/086330
§ 371 (c)(1),
(2) Date: May 30, 2018

(87) PCT Pub. No.: WO2017/099109
PCT Pub. Date: Jun. 15, 2017

(65) Prior Publication Data
US 2018/0346682 A1    Dec. 6, 2018

(30) Foreign Application Priority Data

Dec. 9, 2015 (JP) ................. 2015-240041
Jan. 19, 2016 (JP) ................. 2016-007553

(51) Int. Cl.
C07D 323/04    (2006.01)
C08J 11/16     (2006.01)
(Continued)

(52) U.S. Cl.
CPC ............... *C08J 11/16* (2013.01); *B29B 17/00* (2013.01); *C07D 319/12* (2013.01);
(Continued)

(58) Field of Classification Search
CPC ...... C07D 319/12; C08J 11/16; C08J 2367/04
(Continued)

(56) References Cited

U.S. PATENT DOCUMENTS 5,728,847 A    3/1998    Ohara et al.

FOREIGN PATENT DOCUMENTS

JP    9-77904 A       3/1997
JP    2008-201680 A   9/2008
(Continued)

OTHER PUBLICATIONS

International Search Report of PCT/JP2016/086330 dated Mar. 7, 2017 [PCT/ISA/210].

*Primary Examiner* — Taylor V Oh
(74) *Attorney, Agent, or Firm* — Sughrue Mion, PLLC

(57) ABSTRACT

A method of recovering lactide which includes introducing a molten resin composition that contains a polylactic acid, a depolymerization catalyst and a carrier resin into a vent chamber (3) that is maintained under a reduced pressure using a first screw conveyer passage (11) that extends in the vent chamber (3), gasifying the lactide contained in the molten resin composition, and recovering a gaseous lactide from the vent chamber, wherein a second screw conveyer passage (60) is provided under the first screw conveyer passage (11) in the vent chamber (3) to recover the carrier resin.

9 Claims, 5 Drawing Sheets

(51) Int. Cl.
*B29B 17/00* (2006.01)
*C07D 319/12* (2006.01)

(52) U.S. Cl.
CPC ........... *C08J 2367/04* (2013.01); *Y02W 30/62* (2015.05); *Y02W 30/704* (2015.05); *Y02W 30/705* (2015.05)

(58) Field of Classification Search
USPC ........................................................ 549/274
See application file for complete search history.

(56) References Cited

FOREIGN PATENT DOCUMENTS

| | | | |
|---|---|---|---|
| JP | 2010-126490 | A | 6/2010 |
| JP | 2010-126491 | A | 6/2010 |
| JP | 2012-025855 | A | 2/2012 |
| JP | 5051729 | B2 | 10/2012 |

METHOD OF RECOVERING LACTIDE

CROSS REFERENCE TO RELATED APPLICATIONS

This application is a National Stage of International Application No. PCT/JP2016/086330, filed Dec. 7, 2016, claiming priority based on Japanese Patent Application Nos. 2015-240041 filed Dec. 9, 2015 and 2016-007553 filed Jan. 19, 2016.

TECHNICAL FIELD

This invention relates to a method of recovering lactide that is formed by the depolymerization of a polylactic acid.

BACKGROUND ART

As means for solving the problem of an abnormal increase in the amount of the waste plastic materials due to an increased use of plastic materials in recent years, attention has been given to biodegradable plastic materials that undergo the decay by the action of enzymes which are released out of the bodies of bacteria and Eumycetes. Among these biodegradable plastic materials, the polylactic acid is drawing attention as an aliphatic polyester that is easily available being mass-produced on an industrial scale and that is environmentally friendly. Therefore, its use in various forms has been proposed in a wide range of fields.

The polylactic acid (PLA) is a resin made from such starting cereal starches as corns, and is a product obtained by fermenting starches with the lactic acid, or is a polymer obtained by the direct polycondensation of an L-lactic acid as a monomer, or is a polymer obtained by the ring-opening polymerization of a lactide which is a dimer thereof. The polymer is also drawing attention as a resin of the type of a biologically completely recycling system since it can be decomposed into water and carbonic acid gas by the microorganisms present in the natural world.

As a recycling system of the polylactic acid in recent years, the greatest attention has been paid to a chemical recycling method which is capable of decomposing the polylactic acid and reusing it. This method comprises depolymerizing the polylactic acid by the heating in the presence of a depolymerization catalyst, and subjecting the obtained lactide to the ring-opening polymerization again to reuse it as the polylactic acid.

Patent documents 1 and 2 are proposing apparatuses for recovering the lactide from the polylactic acid that is applied to the chemical recycling. According to the apparatuses proposed by these patent documents, the polylactic acid, the depolymerization catalyst and the carrier resin are thrown into a biaxial extruder and are melt-kneaded therein. The melt-kneaded product is then conveyed by a screw in the biaxial extruder into a vent chamber (vent zone) where the lactide formed by the depolymerization of the polylactic acid is gasified, separated from other components and is recovered. Namely, the lactide of a low molecular weight (which is 144) formed by the depolymerization of the polylactic acid has a boiling point of as high as 255° C. under the standard atmospheric pressure. Therefore, upon feeding a molten kneaded product that contains the polylactic acid and the depolymerization catalyst into the vent chamber maintained under a reduced pressure, the boiling point of the lactide can be lowered, and the lactide that is formed can be recovered in a gasified form.

There is no problem if the lactide is recovered by using the above-mentioned recovering apparatuses on a laboratory scale. A problem, however, arouses if it is attempted to recover the lactide on an industrial scale by throwing the polylactic acid in large amounts.

The following facts have been learned through the study conducted by the present inventors. That is, in the extruder, for instance, the carrier resin is moving while being melted and compressed, and the molten polylactic acid having a small melt viscosity and the depolymerization catalyst are conveyed by the carrier resin. Here, when the molten and compressed carrier resin is introduced into the vent chamber in which the pressure has been reduced, the carrier resin and the depolymerized lactide undergo the expansion since the pressure is reduced, and the carrier resin turns into a resin mass and floats on the screw conveyer passage. If the carrier resin grows into a large resin mass, the molten mixture is covered with the resin mass whereby the lactide is prevented from volatilizing. The resin mass, further, clogs the flow passage of the gaseous lactide formed by the depolymerization of the polylactic acid, and causes a great decrease in the efficiency for recovering the lactide. Moreover, the resin mass scatters and mixes into the lactide that is trapped from the vent chamber causing, therefore, serious problems.

The state where the lactide is allowed to volatilize little or is prevented from volatilizing due to the mass of the carrier resin is, usually, called "vent-up".

The vent up could also be caused by the refluxing of the lactide.

That is, a wall portion (specifically, a cylinder wall forming the screw conveyer passage) in the vent chamber in which the pressure is maintained reduced is heated by a heater, whereby the lactide formed by the depolymerization is gasified and is trapped being separated from the carrier resin and the catalyst. Here, however, the gasified lactide undergoes the condensation upon coming in contact with a peep window (skylight) and with the surfaces of the upper inner wall of a low temperature; i.e., the gasified lactide turns into droplets thereof and often return again onto the screw conveyer passage. If such a refluxing becomes conspicuous, the screws and the surfaces of the cylinder walls are covered with the liquid substance. As a result, the carrier resin (molten resin) undergoes the slipping and no longer moves forward causing the resin mass to grow and the vent-up to occur.

Further, the refluxing phenomenon becomes a process that repeats the gasification and liquefaction, and permits the racemization of the desired lactide to take place. For example, there take place an optical isomeric transition from the L-lactide into the meso-lactide and an optical isomeric transition from the meso-lactide into the D-lactide, causing a decrease in the purity (optical purity) of the obtained L-lactide.

PRIOR ART DOCUMENTS

Patent Documents

Patent document 1: JP-A-2010-126490
Patent document 2: Japanese Patent No. 5051729

Outline of the Invention

Problems that the Invention is to Solve

It is, therefore, an object of the present invention to provide a method of recovering lactide, that is capable of effectively recovering lactide formed by the depolymerization of the polylactic acid while effectively removing the resin masses without permitting the occurrence of vent-up.

Means for Solving the Problems

According to the present invention, there is provided a method of recovering lactide comprising introducing a molten resin composition that contains a polylactic acid, a depolymerization catalyst and a carrier resin into a vent chamber that is maintained under a reduced pressure by using a first screw conveyer passage that is extending in the vent chamber, gasifying the lactide contained in the molten resin composition, and recovering a gaseous lactide from the vent chamber, wherein a second screw conveyer passage is provided under the first screw conveyer passage in the vent chamber to recover the carrier resin.

In the method of recovering lactide of the present invention, it is desired that:
(1) A return member is provided over the first screw conveyer passage to return resin masses formed accompanying the gasification of the lactide back to the first screw conveyer passage;
(2) Second screws extending in the second screw conveyer passage have a diameter SD2 that is set to be smaller than a diameter SD1 of first conveyer screws that are extending in the first screw conveyer passage;
(3) A trapping apparatus is linked to the vent chamber to trap the gaseous lactide;
(4) An upper wall of the vent chamber is provided with a vessel for receiving a refluxing liquid that falls down along the upper wall, the vessel being partitioned from the first screw conveyer passage;
(5) The upper wall of the vent chamber is provided with a tilted peep window;
(6) The second screw conveyer passage is communicated with an extruder for discharging the carrier resin; and
(7) The return member is a fall-down screw provided being engaged with the conveyer screws that are extending in the first screw conveyer passage.

In the method of recovering lactide of the present invention, it is also allowable to provide a return member for returning the resin masses back to the first screw conveyer passage instead of providing the above-mentioned second screw conveyer passage.

Effects of the Invention

According to the method of recovering lactide of the present invention, the screw conveyer passage (second screw conveyer passage) dedicated to discharging the carrier resin contained in the molten resin composition is provided separately from, and under, the screw conveyer passage (first screw conveyer passage) which is for conveying the molten resin composition that contains the polylactic acid. That is, the lactide formed by the decomposition of the polylactic acid is removed in a gaseous form from the molten resin composition that is introduced by the first screw conveyer passage. Therefore, the composition now mostly comprises the carrier resin only and has a greatly reduced volume. Therefore, almost no resin mass develop. Even if resin masses develop, they quickly fall from the first screw conveyer passage down to the second conveyer passage together with the carrier resin, and are discharged by the second conveyer passage.

In the invention, further, a return member can be provided on the first screw conveyer passage to return the resin masses formed accompanying the gasification of the lactide back to the first screw conveyer passage. Namely, in this embodiment, the resin masses that are formed are returned by the return member back to the first screw conveyer passage and are removed. In this case, too, the problem of vent-up caused by the resin masses can be prevented.

In the present invention, therefore, it is allowable to provide both the second screw conveyer passage and the return member, or to provide either the second screw conveyer passage or the return member.

As described above, the present invention quickly removes the carrier resin that might form resin masses and could cause the vent-up from the first conveyer passage. The invention, therefore, effectively suppresses the occurrence or growth of the resin masses and effectively prevents the vent-up caused by the resin masses, i.e., prevents the clogging in the vent chamber as well as such a problem that the resin masses are mixed into the trapped lactide. Therefore, the operation can be stably continued to recover the lactide in a gaseous form maintaining good efficiency and stability, the lactide being obtained in a highly pure form without impurities.

MODES FOR CARRYING OUT THE INVENTION

Figure 1:
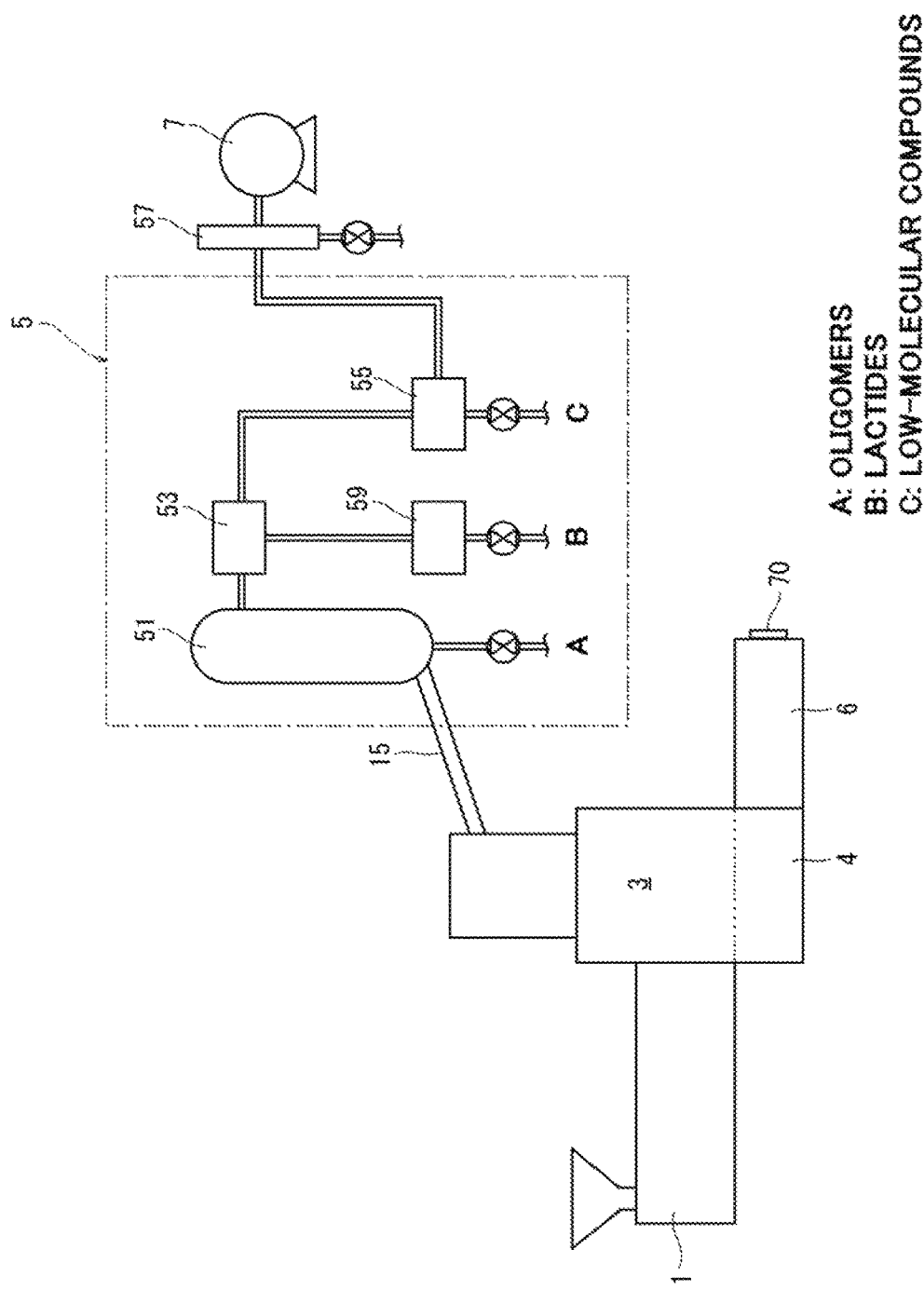
FIG. 1 It is a drawing schematically illustrating the structure of a recovering apparatus used for favorably carrying out a recovering method of the present invention.

Referring to FIG. 1, roughly speaking, a recovering apparatus used for carrying out the method of recovering lactide of the present invention comprises an extruder (melt-kneading apparatus) 1, a vent chamber 3 communicated with the extruder 1, a carrier resin recovering chamber 4 positioned under the vent chamber 3, a trapping apparatus 5 communicated with the vent chamber 3, and an extruder 6 for discharging the carrier resin communicated with the carrier resin recovering chamber. Usually, the interior of the vent chamber 3 is maintained under a predetermined reduced pressure due to a vacuum pump 7 provided on the side of the trapping apparatus 5.

The present invention uses the above-mentioned recovering apparatus. Namely, a polylactic acid, a depolymerization catalyst and a carrier resin are thrown into a hopper of the extruder 1, and are melt-kneaded in a cylinder of the extruder 1 where the polylactic acid is depolymerized. The melt-kneaded product is then fed into the vent chamber 3 where a lactide formed by the depolymerization of the polylactic acid is gasified. The gasified lactide is then introduced into the trapping apparatus 5 that is communicated with the vent chamber 3, is liquefied through a gas-liquid separation tower 51 and a first condenser 53, and is recovered through a receiver 59. The carrier resin, on the other hand, is discharged from the carrier resin recovering chamber 4 under the vent chamber 3 through the extruder 6 for discharging the carrier resin.

As the polylactic acid from which the lactide is to be recovered, there can be used those recovered from the market (post-consumer wastes), industrial wastes discharged from the resin processing manufacturers and out-of-specification resins generated in the step of producing polylactic acid resins. There can be, further, used those of the stereocomplex type in which L-lactic acid (PLLA) and D-lactic acid (PDLA) are mixed together, or those of the meso type in which L-lactic acid unit and D-lactic acid unit are present in a mixed manner in the molecular chains. Use of a virgin polylactic acid poses no problem, as a matter of course.

Moreover, the polylactic acid that is used may include small amounts of copolymer units, e.g., may include units due to lactones, cyclic ethers, cyclic amides, alcohols or carboxylic acids, that are capable of copolymerizing with the lactide under the condition that not less than 50 mol % thereof are the lactic acid units.

MgO is a representative example of the catalyst for depolymerizing the polylactic acid, and is most preferably used. However, there can also be used such alkaline earth metal oxides as CaO, SrO, BaO and the like. There can be, further, preferably used Tin(II)2-ethylhexanoate which is used as the polymerization catalyst and aluminum hydroxide $(Al(OH)_3)$ which is a flame retarder. It is also allowable to use these catalysts as a mixture thereof. The depolymerization catalyst works to lower the temperature for depolymerizing the polylactic acid. Upon using the depolymerization catalyst, thermal decomposition of the polylactic acid is accelerated, and the polylactic acid acquires decreased molecular weights. For instance, the polylactic acid that possessed a molecular weight of about 200,000 when it was thrown into the hopper of the extruder 1 can be decomposed into a lactide of a molecular weight of 144. Further, MgO and the like are effective in suppressing the racemization phenomenon during the thermal reaction.

The catalyst for depolymerizing the polylactic acid is used, usually, in an amount of 0.1 to 5 parts by mass per 100 parts by mass of the polylactic acid.

The carrier resin is used for conveying a melt of the polylactic acid by screw and also works as a sealing material. As the carrier resin, there can be used various thermoplastic resins so far as they do not adversely affect the depolymerization of the polylactic acid and do not show reactivity to the lactide that is formed by the depolymerization of the polylactic acid. Usually, there can be used olefin resins such as polyethylene and polypropylene; polyester resins such as polyethylene terephthalate (PET) and the like; polyethers such as polycarbonate (PC) and the like; and styrol resins such as polystyrene (PS) and the like. Specifically preferably, there can be used HDPE, LDPE and PP having high melt viscosities.

That is, the polylactic acids containing the lactide, in general, have melt viscosities that are considerably lower than those of the ordinary polymers though dependent upon their molecular weights. Therefore, the melt of the polylactic acid cannot be efficiently conveyed by the screw. This is because the screw turns almost empty-loaded. Accordingly, the carrier resin is used in combination to increase the viscosity of the molten resin that contains the melt of the polylactic acid in the extruder. The melt of the polylactic acid can then be efficiently conveyed by screws.

Besides, the carrier resin has a melt viscosity higher than that of the polylactic acid that contains the lactide. By adding the carrier resin in certain amounts to the polylactic acid, and mixing and melting the two together, therefore, the gaps between the inner surface of the cylinder of the extruder and the screws are filled with the molten mixture which, therefore, can be conveyed by screws. Namely, the carrier resin enables the gaps between the inner surface of the cylinder and the screws to be sealed at all times, and the pressure in the vent chamber 3 can be effectively reduced.

It is also allowable to use a carrier resin having a low melt viscosity. That is, the resin (PET, PC, PS or the like) does not by itself undergo the thermal decomposition if it has a thermal decomposition temperature higher than the depolymerization temperature of the PLA, and can be used to convey (move forward) the polylactic acid and the depolymerized product thereof by screws.

In the present invention, the amount of the carrier resin is, usually, set to lie in a suitable range depending on the specifications of the apparatus. For instance, the amount thereof is set to be about 20 to about 10,000 parts by mass and, more preferably, 20 to 100 parts by mass per 100 parts by mass of the polylactic acid from the standpoint of attaining conveyance by screws and vacuum sealing. This amount is considerably smaller than the amounts that are usually employed. The reasons will be described later.

The above-mentioned polylactic acid, depolymerization catalyst and carrier resin are thrown in predetermined amounts into the hopper of the extruder 1, and are melted and mixed together in the cylinder of the extruder 1.

The interior of the cylinder is heated by a heater that is so provided as to cover the cylinder of the extruder 1. The components are melted and mixed together while being stirred and conveyed by the screws that are running in the cylinder, and the polylactic acid is depolymerized at a temperature of not lower than 250° C. As the extruder 1, there is, usually, used a biaxial extruder equipped with two or more screws, and the components are melted and mixed together while heating the interior of the cylinder at 250° C. to 350° C. Accompanying the melting and mixing, the polylactic acid starts depolymerizing, and the molecular weight of the polylactic acid starts decreasing.

The molecular weight of the polylactic acid continues to decrease accompanying the melting and mixing, and there is obtained a lactide (dimer of lactic acid) that forms a basic unit of the polylactic acid. However, the lactide has a boiling point of 255° C. under the standard atmospheric pressure, which is in a boundary temperature region of gas-liquid separation where the gas cannot be trapped maintaining stability. That is, in a state where the lactide remains liquid, the lactide cannot be separated from the molten carrier resin effectively and stably. Therefore, the melt-kneaded product is introduced into the vent chamber 3 in which the pressure is maintained reduced in order to lower the boiling point of the lactide, to accelerate the gas-liquid phase conversion and to accelerate the gasification.

Figure 2:
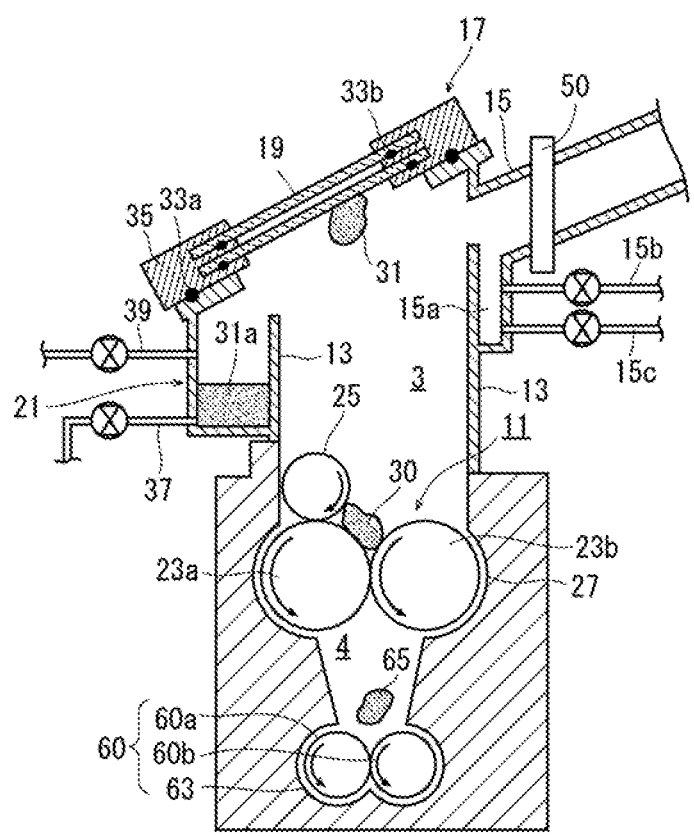
FIG. 2 It is a view illustrating in cross section the structure of a vent chamber in the recovering apparatus of FIG. 1 together with a chamber for recovering a carrier resin.

Referring to FIG. 2 together with FIG. 1, the vent chamber 3 is equipped with a first screw conveyer passage 11. A carrier resin recovering chamber 4 is arranged under the first screw conveyer passage 11. Further, a trapping tube 15 communicated with the trapping apparatus 5 is linked to an upper part of a side wall 13 that is rising up from the first screw conveyer passage 11.

A ceiling wall 17 of the vent chamber 3 has a tilted structure and a peep window 19 is fitted to the tilted portion thereof making it possible to observe, through the peep window 19 at all times, the interior of the vent chamber 3 and, specifically, the state of the first screw conveyer passage 11.

Further, the lower end portion of the peep window 19 is stretching up to a portion on the outer side of the side wall 13 that is rising up from the first screw conveyer passage 11. A vessel 21 for receiving a refluxing liquid is provided on the lower side of the lower end portion of the peep window 19. The receiving vessel 21 is partitioned by the side wall 13 from the first screw conveyer passage 11 so that the refluxing liquid will not return to the screw conveyer passage 11.

In the vent chamber 3 of the above structure, the screw conveyer passage 11 comprises a pair of first conveyer screws 23a and 23b that rotate in the same direction, a fall-down screw 25 suitably arranged over the one first conveyer screw 23a, and a cylinder wall (barrel) 27 that holds the first conveyer screws 23a and 23b.

The cylinder wall 27 is the one that is extending from the cylinder wall of the extruder 1. Similarly, the first conveyer screws 23a and 23b are the ones that are extending from the screws in the extruder 1. Therefore, the molten mixture is conveyed from the extruder 1 toward the front of the surface of the paper in FIG. 2 and is introduced into the vent chamber 3.

In the embodiment of FIG. 2, further, the fall-down screw 25 is provided in the upper part of the first screw conveyer passage 11 so as to work as a return member. The return member is to return the resin masses (designated at 30) formed accompanying the gasification of the lactide back to the first screw conveyer passage 11.

As the return member, the fall-down screw 25 is selectively provided in the vent chamber 3 and is suitably arranged therein. The fall-down screw 25 is in engagement with the first conveyer screw 23a and rotates in a direction opposite to the conveyer screw 23a (but in the same direction at the nipping position).

The pressure in the vent chamber 3 is reduced down to about 0.1 to about 8 kPaA by the operation of a vacuum pump 7. Due to a heater (not shown) provided in the cylinder wall 27, further, the interior of the first screw conveyer passage 11 is heated to about 250° C. to about 350° C. like in the cylinder portion in the extruder 1. Therefore, the lactide is gasified as it is formed by the depolymerization of the polylactic acid contained in the molten mixture that is introduced into the vent chamber 3 by the first conveyer screws 23a, 23b extending in the first screw conveyer passage 11. The gasified lactide is then introduced into the trapping apparatus 5 through the trapping tube 15.

Here, the molten mixture conveyed by the screws contains a depolymerized product of polylactic acid having a high vapor pressure, and is introduced in a compressed state into the vent chamber 3 in which the pressure has been reduced. Therefore, the molten mixture expands in the vent chamber 3 and often forms resin masses 30 in a state of being floated over the first conveyer screws 23a and 23b. If the operation of the recovering apparatus is continued, therefore, the resin masses 30 are often formed continuously floating over the pair of first conveyer screws 23a and 23b in the vent chamber 3. The resin masses 30 are like a scab formed chiefly of the carrier resin. The resin masses 30 that grow large could clog and hinder the recovery of the lactide gas. Moreover, the scattered resin masses 30 could enter into the trapping apparatus 5 through the trapping tube 15, and could close the whole trapping tube 15. That is, the vent-up takes place.

As will be understood from FIG. 2, the fall-down screw 25 is provided over the first conveyer screw 23a, and rotates in a direction opposite to the first conveyer screw 23a. Therefore, the resin masses 30 floating over the first screw conveyer passage 11 are returned by the fall-down screw 25 again back to the first screw conveyer 23a and, thereafter, fall on a second screw conveyer passage 60 so as to be discharged together with the carrier resin.

As described above, the fall-down screw 25 works as the return member for returning the resin masses 30 back to the first screw conveyer passage 11, whereby the resin masses 30 are suppressed from growing effectively preventing inconveniences caused by the growth of the resin masses 30.

The turn of the fall-down screw 25 that is used as the return member may or may not be in synchronism with the turn of the first conveyer screws 23a and 23b.

The vent-up could occur if the gasified lactide is cooled and liquefied (i.e., refluxed) again upon contacting to the peep window 19 and the like. However, the vent chamber 3 of the above-mentioned structure is capable of effectively preventing inconveniences caused by the refluxing liquid of lactide.

That is, if the molten mixture containing the polylactic acid, depolymerization catalyst and carrier resin is introduced from the extruder 1 into the vent chamber 3 by the first screw conveyer passage 11 so as to continuously gasify the lactide, then liquid droplets 31 (i.e., refluxed liquid) are often formed being condensed on the surface of the peep window 19. The liquid droplets 31 that fall on the first screw conveyer passage 11 could form a liquid film so as to cover the surfaces of the first conveyer screws 23a, 23b running in the conveyer passage 11 or to cover the inner surfaces of the cylinder wall 27. Therefore, the molten mixture tends to undergo slipping and, as a result, the resin masses 30 are easily formed.

With the vent chamber 3 of the structure shown in FIG. 2, on the other hand, the peep window 19 is provided in a tilted manner, the liquid droplets 31 formed by condensation flow down along the surface of the peep window 19 and are contained in the receiving vessel 21 that is completely partitioned by the side wall 13 from the first screw conveyer passage 11. That is, it is made possible to effectively alleviate such an inconvenience that the liquid droplets 31 fall on the first screw conveyer passage 11 accelerating the occurrence of resin masses 30.

Further, the liquid droplets 31 that fall on the first screw conveyer passage 11 cause the gasification and liquefaction of the lactide in a recurring manner, accelerate the racemization of the lactide and, therefore, cause a degree in the optical purity of the lactide that is obtained. With the vent chamber 3 of the above-mentioned structure, however, the above inconvenience, too, can be effectively alleviated.

It is desired that the peep window 19 is a double window as shown in FIG. 2, and is fitted to the ceiling wall 17 using gaskets 35 provided with O-rings 33a and 33b. This structure enables the peep window 19 to possess improved heat retaining property and to prevent the condensation, and hence formation of the refluxing liquid can be effectively alleviated.

The receiving vessel 21 for trapping the liquid droplets 31 (refluxing liquid) is provided in the bottom portion thereof with a recovering line 37 for recovering the refluxing liquid 31a that is collected in the receiving vessel 21. At an upper part of the side wall of the receiving vessel 21, there is provided a vacuum break/restore line 39 for holding a degree of vacuum in the vent chamber 3 or for breaking the vacuum therein. Due to this structure, the refluxing liquid 31a collected in the receiving vessel 21 can be recovered.

Figure 3:
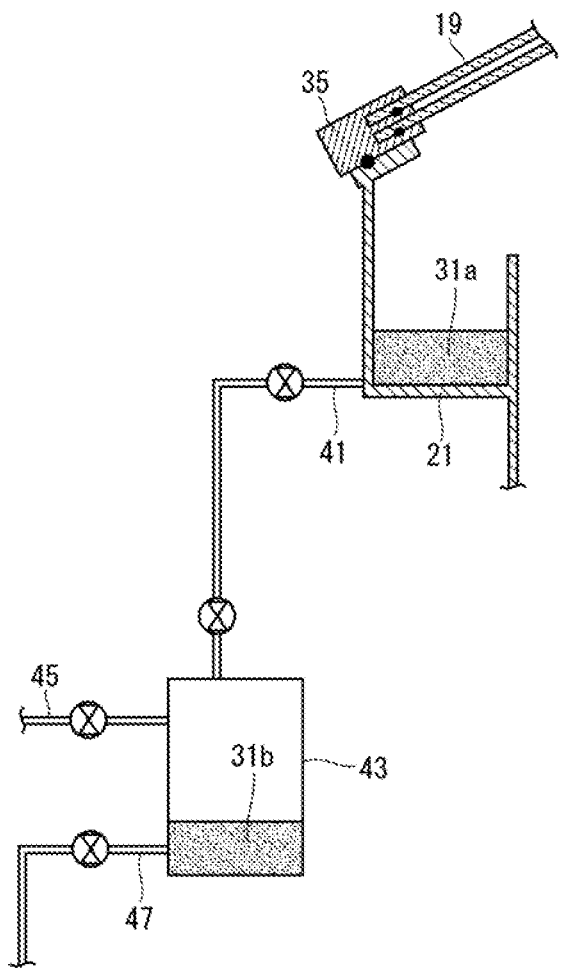
FIG. 3 It is a view schematically illustrating another structure of a receiving vessel provided in the vent chamber of FIG. 2.

The structure of the receiving vessel 21 is not limited to the one shown in FIG. 2 but may be the one as shown in FIG. 3. Namely, a temporary trapping vessel 43 is linked to the bottom of the receiving vessel 21 via a trapping line 41. The temporary trapping vessel 43 is provided with a vacuum break/restore line 45 and a recovery line 47. The refluxing liquid 31a collected in the receiving vessel 21 is then moved into the temporary trapping vessel 43 via the trapping line and is recovered without breaking the vacuum system in the vent chamber 3.

The lactide gasified in the vent chamber 3 is introduced into the trapping apparatus 5 via the trapping tube 15 provided at the upper part of the side wall 13. Here, as shown in FIG. 2, the trapping tube 15 is extending being tilted upward and is, further, provided with a vacuum break prevention valve 50 which will be opened or closed in case of abnormal condition.

It is, further, desired that the inlet portion of the trapping tube 15, too, is provided with a receiving vessel 15a for receiving the refluxing liquid. That is, it is desired that the refluxing liquid liquefied in the trapping tube 15 is trapped by the receiving vessel 15a and is prevented from flowing down into the screw conveyer passage 11. The receiving vessel 15a, too, is provided with a vacuum break/restore line 15b and a recovering line 15c.

In the trapping apparatus 5 to which the trapping tube 15 is linked, there are provided a gas-liquid separation column 51, a first condenser 53, a second condenser 55 and a chilling trap 57. Impurities are removed by gas-liquid separation from the gaseous product of lactide collected from the vent chamber 3, and the lactide is recovered in a highly pure form. That is, the gaseous product of lactide collected from the vent chamber 3 contains various low molecular compounds derived from oligomers of lactic acid and polymerization initiator contained in the polylactic acid or the carrier resin, in addition to containing the lactide. Therefore, these impurities must be removed.

Concretely, the lactide recovered in a gaseous form is passed through the gas-liquid separation column (rectification column) 51 to remove high molecular oligomer components through the demister in the gas-liquid separation column. Thereafter, the lactide is introduced into the first condenser (heat exchanger) 53 where the lactide only is subjected to the phase conversion (phase change) so as to be recovered as liquid lactide.

A proper heat-exchange temperature in the phase conversion varies depending on the degree of vacuum. Usually, under the standard atmospheric pressure, the lactide (L-lactide/D-lactide) has a boiling point and a melting point which are, respectively, 255° C. and 92° C. to 94° C. Therefore, the heat-exchange temperature is, preferably, 60° C. to 140° C. in a vacuum range of 0.1 KPaA to 8 KPaA. More preferably, the heat-exchange temperature is 80° C. to 90° C. in a vacuum range of 0.5 KPaA to 4 KPaA.

If lower than 0.1 KPaA, for example, the degree of vacuum is so high that the resin masses are formed much, and the vent-up takes place easily. If higher than 8 KPaA, on the other hand, the degree of vacuum is so low that the boiling point of the lactide is not lowered to a sufficient degree, the lactide is not gasified to a sufficient degree, and the lactide recovering efficiency tends to decrease.

If the heat-exchange temperature is lower than the above range, further, the low-boiling impurities tend to be liquefied, and the purity of the recovered lactide may decrease. If the heat-exchange temperature is higher than the above range, on the other hand, the lactide is not easily liquefied and, therefore, tends to be recovered at a decreased efficiency.

Further, in order to recover the depolymerized product (lactide) of the polylactic acid in the gaseous form, it is desired that the facilities (gas-liquid separation column 51, first condenser 53, second condenser 55, etc.) in the trapping apparatus 5 are installed at positions higher than the vent chamber 3.

The gas from which the oligomers are removed is cooled through the first condenser (heat exchanger) 53 down to about 80° C. whereby the desired lactide is liquefied and is recovered in the receiver 59. The remaining gas is cooled through the second condenser (heat exchanger) 55 down to about 5° C. whereby low-boiling low-molecular compounds are removed. Finally, the gas is cooled through the chilling trap 57 down to about −50° C., and the residual compounds, too, are removed in the form of a liquid.

The refluxing liquid 31a collected in the receiving vessel 21 and the liquid collected in the bottom portion of the receiving vessel 15a provided in the trapping tube 15, can be directly discarded. Or, if there is no problem, these liquids can be introduced into the step of refining together with the liquid lactide recovered in the receiver 59.

As described above, the molten resin composition containing the polylactic acid and the carrier resin is fed into the vent chamber 3 by using the first screw conveyer passage 11 (first conveyer screws 23a, 23b), and the lactide formed by the depolymerization of the polylactic acid is gasified in the vent chamber 3 and is recovered by the trapping apparatus 5. In this case, the volume of the molten resin composition conveyed by the first screw conveyer passage 11 decreases greatly as the lactide is gasified.

In the present invention, the residue 65 of the molten resin composition (mostly, the carrier resin) from which the lactide has been removed in the form of a gas, is not discharged through the first screw conveyer passage 11 but is discharged through a carrier resin recovering chamber 4 provided under the vent chamber 3.

That is, in the carrier resin recovering chamber 4 as shown in FIG. 2, a second screw conveyer passage 60 is provided for recovering the carrier resin at a position under the first screw conveyer passage 11 of which the one end is closed. The resin mass 65 (carrier resin) fallen down from the first screw conveyer passage 11 is discharged by the second screw conveyer passage 60.

In the above-mentioned first screw conveyer passage 11, for instance, the cylinder wall 27 on the lower side of the first conveyer screws 23a, 23b is at least partly opened and is communicated with the second screw conveyer passage 60.

The second conveyer passage 60 comprises a pair of second conveyer screws 60a and 60b that rotate in the same direction, and a cylinder wall 63 surrounding the second conveyer screws 60a and 60b.

The second screw conveyer passage 60, as shown in FIG. 2, is communicated with the extruder 6 for discharging the carrier resin that is extending in the same direction as the conveyer passage 60 in order to efficiently discharge the carrier resin yet maintaining the degree of vacuum in the vent chamber 3.

Figure 4:
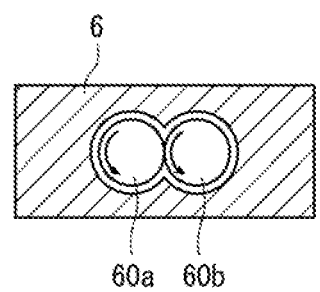
FIG. 4 It is a view illustrating in cross section an extruder for discharging the carrier resin, the extruder extending in a second screw conveyer passage in the recovering apparatus of FIG. 1.

That is, as shown in FIG. 4, the second conveyer screws 60a and 60b are extending in the cylinder of the extruder 6 for discharging the carrier resin, and their ends in the feeding direction are extending up to a discharge port 70 provided in the extruder 6.

FIG. 2 and other drawings are not showing the motors for driving the screws in the extruders 1 and 6.

In the above-mentioned structure, the lactide formed by the depolymerization of the polylactic acid is gasified and is removed from the melt of resin on the first screw conveyer passage 11, and the resin mass (carrier resin) 65 which is the residue of the melt of resin falls from the first conveyer passage 11 on the second screw conveyer passage 60.

In the above-mentioned method of the present invention, the carrier resin (i.e., material that could become a cause of resin masses 30) remaining on the first screw conveyer passage 11 is allowed to quickly fall on the second screw conveyer passage 60 dedicated to conveying the carrier resin, and is discharged. It is, therefore, made possible to effectively suppress the formation of the resin masses 30 on the first screw conveyer passage 11 and hence to effectively prevent the occurrence of the vent-up caused by the growth of the resin masses 30.

In the present invention, it is desired that a diameter SD2 of the second conveyer screws 60*a*, 60*b* extending in the second screw conveyer passage 60 is set to be smaller than a diameter SD1 of the first conveyer screws 23*a*, 23*b*.

That is, the molten carrier resin arrives at the second screw conveyer passage 60 and is conveyed by the second conveyer screws 60 and 60*b*. Thereafter, the molten carrier resin is melt-extruded from the discharge port 70 through the extruder 6 for discharging the carrier resin. To maintain the degree of vacuum in the vent chamber 3, in this case, the amount of the carrier resin must be secured so that the vacuum sealing is maintained in the extruder 6 for discharging the carrier resin. Here, by decreasing the diameter SD2 of the second conveyer screws 60*a*, 60*b*, the volume of gap decreases between the screws 60*a*, 60*b* and the surrounding cylinder wall. As a result, the vacuum sealing can be maintained by using the carrier resin in a decreased amount. As compared to the case where the second screw conveyer passage 60 has not been provided and the carrier resin is discharged from the first screw conveyer passage 11, therefore, it is made possible to depolymerize the polylactic acid with a resin composition that contains the carrier resin at a decreased ratio.

According to the present invention as described above, it is desired that the diameter SD2 of the second conveyer screws 60*a*, 60*b* is smaller than the diameter SD1 of the first conveyer screws 23*a*, 23*b*. The diameter ratio SD2/SD1 is, more preferably, in a range of 0.25 to 0.90 and, further preferably, in a range of 0.35 to 0.80.

If the diameter ratio SD2/SD1 is smaller than the above range, the amount of the carrier resin falling on the second screw conveyer passage 60 may surpass the amount that is discharged by the second conveyer screws 60*a* and 60*b*. The carrier resin can be discharged in an increased amount by increasing the rotational speed of the second conveyer screws 60*a* and 60*b*, as a matter of course. In this case, however, a too increased load may be exerted on the apparatus which, therefore, may be damaged or its service life may be shortened. If the diameter ratio SD2/SD1 is larger than the above range, on the other hand, the advantage of using the carrier resin in a decreased amount cannot be utilized to a sufficient degree and, besides, the vacuum sealing may become defective.

In the invention described above, the second screw conveyer passage 60 comprises a pair of conveyer screws 60*a* and 60*b*. So far as the resin masses 65 can be conveyed and effectively discharged from the discharge port 70, however, there may be employed only one conveyer screw.

Figure 5:
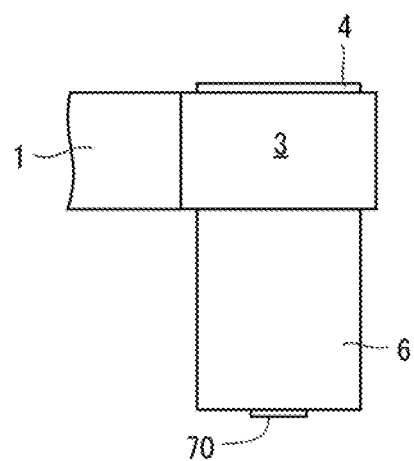
FIG. 5 It is a schematic plan view illustrating another example of the positional relationship between the vent chamber and the extruder for discharging the carrier resin shown in FIG. 1.

In the embodiment shown in FIGS. 1 and 2, the second screw conveyer passage 60 (second conveyer screws 60*a*, 60*b*) is extending in the same direction as the first screw conveyer passage 11 (conveyer screws 23*a*, 23*b*). As will be learned from FIG. 5 which is a schematic plan view of the structure, however, it is also allowable to provide the second screw conveyer passage 60 (conveyer screws 60*a*, 60*b*) in a direction at right angles with the first screw conveyer passage 11 (conveyer screws 23*a*, 23*b*) but still being communicated with the extruder 6 for discharging the carrier resin.

The carrier resin is discharged from the discharge port 70 provided at an end of the second screw conveyer passage 60 in the direction of feed. The carrier resin can be directly discarded but, as required, may be reused, i.e., may be mixed with the polylactic acid and may be fed again to the extruder 1.

In carrying out the method of recovering lactide of the present invention, the recovering apparatus can be designed in a variety of different ways. As the return member for returning the resin masses 30 to the first screw conveyer passage 11, for instance, there can be used a member different from the fall-down screw 25.

Figure 6:
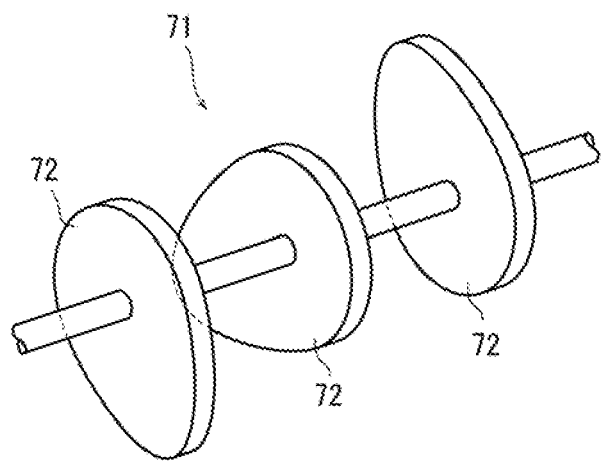
FIG. 6 It is a view schematically illustrating another embodiment of the return member provided in the vent chamber shown in FIG. 2.

As shown in FIG. 6, for example, it is allowable to use, as the return member, a rotary shaft 71 having a plurality of elliptic vanes 72 arranged thereon instead of using the screw blade. That is, by running the rotary shaft 71 in parallel with the first conveyer screw 23*a* or 23*b* and by bringing the rotary shaft 71 into point contact with the first conveyer screw 23*a* or 23*b*, the resin masses 30 can be pushed into the first screw conveyer passage 11. In this embodiment, the area of contact with the molten resin or the time of contact with the molten resin can be decreased offering an advantage of very decreased hindrance against conveying the molten resin.

The fall-down screw 25 used as the return member and the rotary shaft 71 may rotate in, or out of, synchronism with the first conveyer screws 23*a* and 23*b*.

It is, further, allowable to provide a plate-like return member or a point-contact return member so as to cover the upper side of the first conveyer screw 23*a* and/or 23*b* so will not to hinder the flow passage through which the lactide flows into the trapping tube 15 after having been gasified from the molten mixture conveyed by the screws 23*a* and 23*b*.

Figure 7:
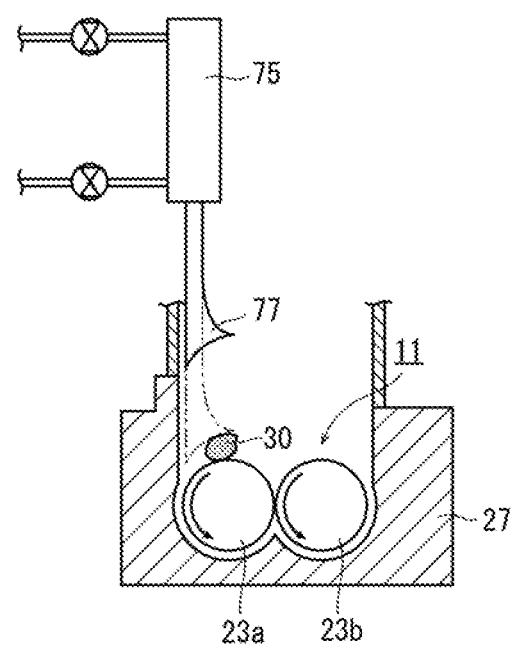
FIG. 7 It is a view schematically illustrating a further embodiment of the return member provided in the vent chamber shown in FIG. 2.

Referring, for example, to FIG. 7, a push plate 77 is moved up and down along the side wall 13 by using an air cylinder 75 to push the resin masses 30 into the first screw conveyer passage 11. In FIG. 7, the second screw conveyer passage 60 is omitted.

In FIG. 7, the lower end surface of the plate 77 has been curved to efficiently push the masses. To prevent the molten resin from adhering, further, it is desired that a highly smooth nonpolar film is formed on the lower end surface of the plate 77 by, for example, forming a film of sintered zirconia on the lower end surface, depositing the DLC on the lower end surface, or forming a Teflon (registered trademark) film on the lower end surface.

According to the present invention, as described above, it is made possible to effectively avoid the problem of vent-up caused by the resin masses 30 formed in the vent chamber 3 and, therefore, to stably operate the apparatus and to continuously recover the lactide of a high purity from the polylactic acid maintaining stability.

Moreover, the amount of the carrier resin that is used can be greatly decreased (e.g., halved) as compared to the case where the first screw conveyer passage 11 is not closed at its one end and the carrier resin is discharged from the end thereof.

In the present invention, further, it is also allowable to remove the resin masses 30 without providing the second screw conveyer passage 60 but by providing only the return member (see FIGS. 2, 6 and 7) over the first screw conveyer passage 23. When the second screw conveyer passage 60 is omitted, the carrier resin and the resin mass 30 are discharged from an end portion of the first screw conveyer passage 23.

DESCRIPTION OF REFERENCE NUMERALS

1: extruder
3: vent chamber
4: carrier resin recovering chamber
5: trapping apparatus
6: extruder for discharging the carrier resin
7: vacuum pump
11: first screw conveyer passage
15: trapping tube
19: peep window
21: receiving vessel
23a, 23b: first conveyer screws
25: fall-down screw
27: cylinder wall
51: gas-liquid separation column
53: first condenser
55: second condenser
60: second screw conveyer passage
60a, 60b: second conveyer screws
63: cylinder wall
65: molten resin residue (carrier resin mass)
70: discharge port

The invention claimed is:

1. A method of recovering lactide comprising introducing a molten resin composition that contains a polylactic acid, a depolymerization catalyst and a carrier resin into a vent chamber that is maintained under a reduced pressure by using a first screw conveyer passage that is extending in the vent chamber, gasifying the lactide contained in said molten resin composition, and recovering a gaseous lactide from said vent chamber, wherein a second screw conveyer passage is provided under said first screw conveyer passage in said vent chamber to recover the carrier resin.

2. The method according to claim 1, wherein a return member is provided over said first screw conveyer passage to return resin masses formed accompanying the gasification of the lactide back to said first screw conveyer passage.

3. The method according to claim 1, wherein second conveyer screws extending in said second screw conveyer passage have a diameter SD2 that is set to be smaller than a diameter SD1 of first conveyer screws that are extending in said first screw conveyer passage.

4. The method according to claim 1, wherein a trapping apparatus is linked to said vent chamber to trap said gaseous lactide.

5. The method according to claim 1, wherein an upper wall of said vent chamber is provided with a vessel for receiving a refluxing liquid that falls down along said upper wall, said vessel being partitioned from said first screw conveyer passage.

6. The method according to claim 5, wherein the upper wall of said vent chamber is provided with a tilted peep window.

7. The method according to claim 1, wherein said second screw conveyer passage is communicated with an extruder for discharging the carrier resin.

8. The method according to claim 2, wherein said return member is a fall-down screw provided being engaged with the conveyer screws that are extending in said first screw conveyer passage.

9. A method of recovering lactide comprising introducing a molten resin composition that contains a polylactic acid, a depolymerization catalyst and a carrier resin into a vent chamber that is maintained under a reduced pressure by using a screw conveyer passage that is extending in the vent chamber, gasifying the lactide contained in said molten resin composition, and recovering a gaseous lactide from said vent chamber, wherein a return member is provided over the screw conveyer passage to return the resin masses formed accompanying the gasification of said lactide back to said screw conveyer passage.

* * * * *